United States Patent
Appling et al.

(10) Patent No.: US 6,287,333 B1
(45) Date of Patent: Sep. 11, 2001

(54) FLEXIBLE STENT

(75) Inventors: William M. Appling, Hartford; Laura Jane Tavormina, Queensbury, both of NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 09/268,112

(22) Filed: Mar. 15, 1999

(51) Int. Cl.$^7$ ............................................. A61F 2/06
(52) U.S. Cl. .............................. 623/1.22; 623/1.15
(58) Field of Search .................... 623/1.15, 1.16, 623/1.17, 1.22; 606/191, 192, 194, 195, 198

(56) References Cited

U.S. PATENT DOCUMENTS

| | | |
|---|---|---|
| 4,733,665 | 3/1988 | Palmaz . |
| 4,856,516 | 8/1989 | Hillstead . |
| 4,886,062 | 12/1989 | Wiktor . |
| 4,922,905 | 5/1990 | Stecker . |
| 4,994,071 | 2/1991 | MacGregor . |
| 5,019,090 | 5/1991 | Pinchuk . |
| 5,133,732 | 7/1992 | Wiktor . |
| 5,135,536 | 8/1992 | Hillstead . |
| 5,161,547 | 11/1992 | Tower . |
| 5,195,984 | 3/1993 | Schatz . |
| 5,217,483 | 6/1993 | Tower . |
| 5,366,504 | 11/1994 | Anderson et al. . |
| 5,389,106 | 2/1995 | Tower . |
| 5,507,767 | 4/1996 | Maeda et al. . |
| 5,591,198 | 1/1997 | Boyle et al. . |
| 5,618,298 | 4/1997 | Simon . |
| 5,643,339 | 7/1997 | Kavteladze et al. . |
| 5,843,120 | 12/1998 | Israel et al. . |
| 5,843,168 | 12/1998 | Dang . |

*Primary Examiner*—David J. Isabella
(74) *Attorney, Agent, or Firm*—Reed Smith LLP

(57) ABSTRACT

A radially expandable flexible body lumen stent is composed of a series of longitudinally adjacent cylindrical wraps. Each wrap is defined by a continuous wire that forms a plurality of loops. The longitudinally adjacent wraps are connected to one another by selected ones of the loops of each wrap engaging loops of an adjacent wrap. This limited coupling between wraps provides restraint on the longitudinal motion of the wraps relative to one another yet maintains stent flexibility so that the stent can be passed through and/or positioned in tortuous lumens of the body.

20 Claims, 9 Drawing Sheets

FLEXIBLE STENT

BACKGROUND OF THE INVENTION

This invention relates in general to a stent and more particularly to a stent that is designed to be particularly flexible so as to navigate tortuous zones of the vascular system while retaining sufficient structural integrity to perform an effective stent function.

A wide variety of stents have been proposed and a number are in use. A major function of stents is as vascular stents which are implanted in the vascular system to hold back obstructions (such as plaque and thrombus) so as to provide ready passage of blood through the lumen. These are employed in percutaneous transluminal vascular angioplasty.

Many stents lack sufficient flexibility to navigate tortuous lumens or to be adequately positioned within a tortuous lumen. This is one of the major limitations on the stent shown in the Palmaz U.S. Pat. No. Re 4,739,762.

There are other stents which have substantial flexibility that permit navigating through tortuous lumens such as the stent described in U.S. Pat. No. 5,217,483. issued to Allen J. Tower. The Tower stent uses a sinusoid shaped wire to form the stent. This geometry is naturally more flexible than articulated or expanding segment stents. Such a similar construction is also described in U.S. Pat. No. 5,019,090 by Pinchuk, and in U.S. Pat. No. 4,886,062 by Wiktor. However, such stents have a tendency to expand in a longitudinal direction, particularly when placed in a tortuous lumen. The result is to lose coverage and thus fail to prevent restenosis in the uncovered areas.

When certain stents are placed within a curve and expanded, gaps appear in the stent structure on the outside of the curve. If the stent is expanded in an area with calcified plaque, the plaque can separate the stent segments allowing the plaque to protrude into the lumen. This is called plaque prolapse.

Another problem with some stent designs is that they are weak and can be easily disrupted by guide wire and catheter manipulation. Stents that can negotiate tortuous curves are not good for supporting lesions in these curves because of the weakness which allows the flexibility.

The need to obtain a stent which is highly flexible but which does not expand or contract in a longitudinal direction when placed in position is recognized and has been addressed for example in U.S. Pat. No. 5,843,168 issued to Kenny L. Dang.

However, experience shows there is difficulty in obtaining the appropriate lumen sidewall coverage in a highly flexible stent that maintains its longitudinal structural integrity.

The trade-off between flexibility and structural integrity or robustness is unsatisfactory in many applications. What is required is a structure or geometry for the stent which preserves a high degree of flexibility with a high degree of longitudinal structural integrity. In spite of many proposals and approaches, there is a present need for a stent that achieves a better combination of these two operational requirements.

Accordingly, it is a primary purpose of this invention to provide a stent that has an enhanced combination of flexibility and longitudinal structural integrity.

It is a related purpose of this invention to provide a device which achieves the above result in a fashion that avoids complex insertion and placement procedures.

It is a further object of this invention to provide a stent achieving the above objectives which provides adequate interior lumen area coverage when placed in position.

Another object is to provide a flexible stent which will have sufficient radial stiffness (hoop strength) to maintain its expanded state yet avoid longitudinal collapse when the placement balloon is withdrawn.

A further object is to provide a stent with a minimal profile so that small diameter body lumens can be traversed and accessed.

BRIEF DESCRIPTION

In brief, one embodiment of this invention involves a stent which is formed from a single wire having a diameter of for example 5 to 10 mils (0.12 to 0.25 mm). This wire is shaped to provide a continuous series of loops which are close enough to one another so that the loops are tear drop shaped rather than, for example, sinusoidal. The band of tear drop shaped loops is wrapped around a cylinder so as to form the basic cylindrical stent.

This stent has a series of 360 degree wraps which are continuous with one another. This basic design is similar to that shown in the Tower design mentioned above. However, in this invention, at least one of the loops of each wrap is coupled through one of the loops of an adjacent wrap. This engagement between adjacent loops of the wraps aids in resisting having the individual wraps spread apart when positioned in a body lumen. Depending upon the diameter of the stent, the number of engaging loops of any wrap may be one, two, three or perhaps even four.

In addition, it has been found useful to have one end of the wire out of which the stent is created extend longitudinally along the cylindrical body of the stent to act as a spine. This spine portion of the wire is woven between loops of adjacent wraps thereby providing additional longitudinal rigidity by virtue of some degree of frictional contact plus the fact that the longitudinal ends of the spine are tied to end loops or wraps to maintain longitudinal stent length.

It is important that the overlap of the loops be minimized so as to reduce friction with the delivery sheath. Accordingly, the loops which do interengage are designed to have slightly larger amplitude than the rest of the loops in the wrap by an amount that is at least the thickness of the wire. This prevents the unlinked loops from overlapping. This serves to optimize the profile of the stent within the lumen where it is placed.

BRIEF DESCRIPTION OF THE DRAWINGS

FIG. 1 is a plan view of a first embodiment of a linked loop stent illustrating two longitudinal rows of linked loop connections.

FIG. 2 is a plan view illustrating the opposite side of the FIG. 1 stent showing the woven longitudinal wire which forms a spine.

FIG. 3 is a schematic showing of a first stage of wire forming to provide a series of "U" shaped waves. FIG. 3 is a segment of the entire strip.

FIG. 4 is a schematic showing of the FIG. 3 segment pinched together to form a segment of a ribbon having a plurality of loops.

FIG. 5 is a schematic illustration of the beginning of the process of wrapping the FIG. 4 ribbon on a mandrel.

FIG. 6 is an enlarged schematic showing the end knot on a first end of the stent. FIG. 6, like FIGS. 8, 9, 16, 17 and 18, show open wire ends because continuations of the wire segments shown are omitted in order to aid in visualizing the feature illustrated.

FIG. 7 is an enlarged schematic showing of the longitudinal wire segment woven through the loops to provide a longitudinal spine for the stent.

FIG. 8 is an enlarged schematic showing linked loops.

FIG. 9 is an enlarged schematic showing the end knots on the second end of the stent.

FIG. 10 is a plan view illustrating the helically wrapped stent of FIG. 1 in its expanded form on a balloon catheter showing two longitudinal rows of linked loop connections.

FIG. 11 is a plan view illustrating the opposite side of the FIG. 10 illustration and shows the woven longitudinal wire which forms a spine.

FIG. 12 is a plan view of a second embodiment of the linked loop stent of the invention illustrating one longitudinal row of linked loop connections.

FIG. 13 is a plan view illustrating the opposite side of the FIG. 12 stent showing the longitudinal wire woven through a line of loops to provide a longitudinal spine for the stent.

FIG. 14 is a schematic showing of a series of stepped ribbon segments used to create the FIG. 12 embodiment.

FIG. 15 is an enlarged schematic showing of a small segment of the stepped ribbon used to create the FIG. 12 embodiment.

FIG. 16 is an enlarged schematic showing an end knot at a first end of the stent.

FIG. 17 is an enlarged schematic showing the woven longitudinal wire.

FIG. 18 is an enlarged schematic showing end knots at a second end of the stent.

FIG. 19 is a plan view illustrating the circular wrapped stent in its expanded form on a balloon catheter showing the woven longitudinal wire which forms a spine.

FIG. 20 is a plan view illustrating the opposite side of the FIG. 19 illustration showing the one row of linked loop connections.

DESCRIPTION OF THE PREFERRED EMBODIMENTS

The First Stent Embodiment

A first embodiment, which might be termed a helical wrap embodiment, is shown in FIGS. 1 through 11. As shown therein, a multi-wrap expandable stent 30 is composed of cylindrical wraps arranged in a helical fashion.

The wraps are formed from a continuous wire which is bent to create a plurality of curved loops 34. The loops 34 of each wrap 32 are adjacent to the loops of adjacent wraps with the exception of certain loops that are engaged.

Figure 1:
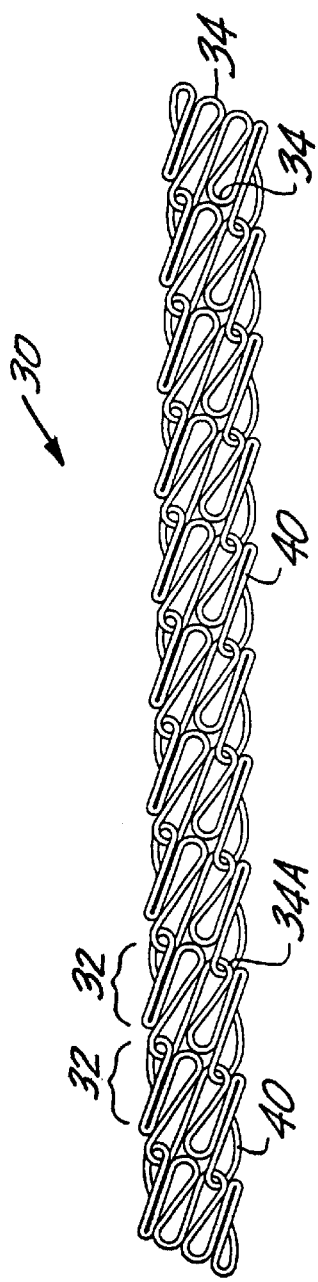
FIGS. 1 through 11 illustrate a helically wrapped linked loop stent.

In the embodiment shown in FIG. 1, certain loops 34A of one wrap 32 engage or are linked to loops 34A of an adjacent wrap 32. Two such loops 34A in each wrap 32 are engaged in the embodiment shown.

The FIG. 1 stent 30 has eleven wraps 32, each wrap being 360°. The wraps 32 are helically arranged and formed from a single wire 40. A loop 34 is considered to be a single tear-drop or U-shape of bent wire 40.

Figure 2:
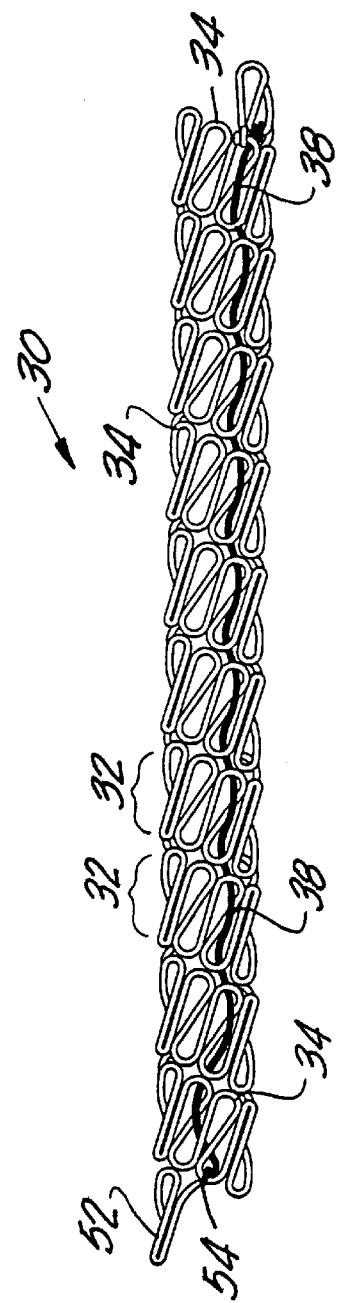

All of the loops 34 of all of the wraps 32 are formed from a single wire 40 and are formed in a fashion indicated below. One extensive end segment 50 of this continuous wire is threaded through a set of longitudinally aligned loops to form a longitudinal spine 38. The spine 38 in FIG. 2 is shown in solid format to have it stand out relative to the rest of the wire. It should be understood that it is the same wire that forms the wraps 32. Each end of the spine 38 is knotted to a loop 34 at opposite ends of the stent.

The structure of the stent shown in FIGS. 1 and 2 can be best understood by tracing through the sequence of steps used in forming the stent. A straight wire 40 has a diameter typically between 0.12 mm and 0.25 mm. One of the known types of wires used for stents is employed such as a platinum alloy wire, tantalum wire or a stainless steel wire.

Figure 3:
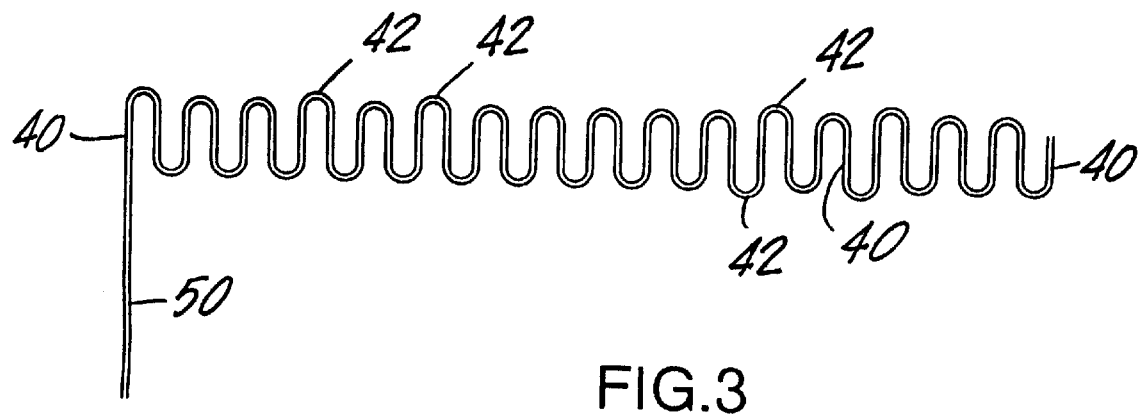
Figure 4:
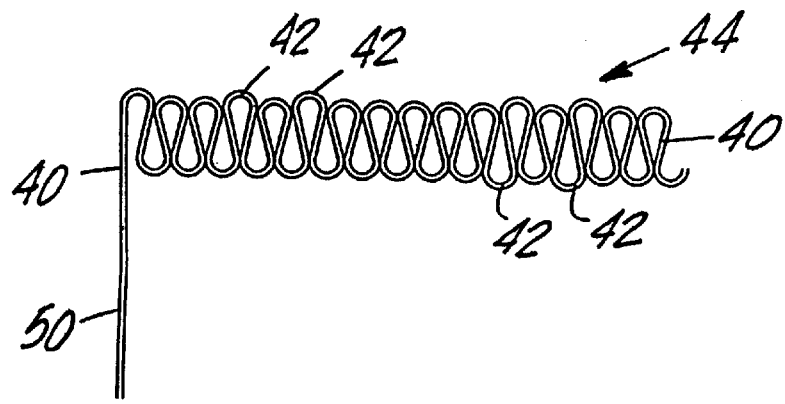

As shown in FIG. 3, the wire is formed into a U-shaped wave pattern. This is presently done on a forming block having a series of grooves within which the wire is bent. The height or amplitude of the waves in most embodiments are from 70 to 160 mils (approximately 1.8 to 4.0 mm). Certain predetermined ones of the waves, such as shown at 42, will have a slightly greater amplitude of at least one wire diameter. This greater amplitude is to enable loop engagement at a later step. These U-shaped waves are then drawn together manually with the use of tweezers to form a ribbon 44, a segment of which is shown in FIG. 4. The greater amplitude waves 42 can be more clearly seen in FIG. 4 than in FIG. 3.

Figure 5:
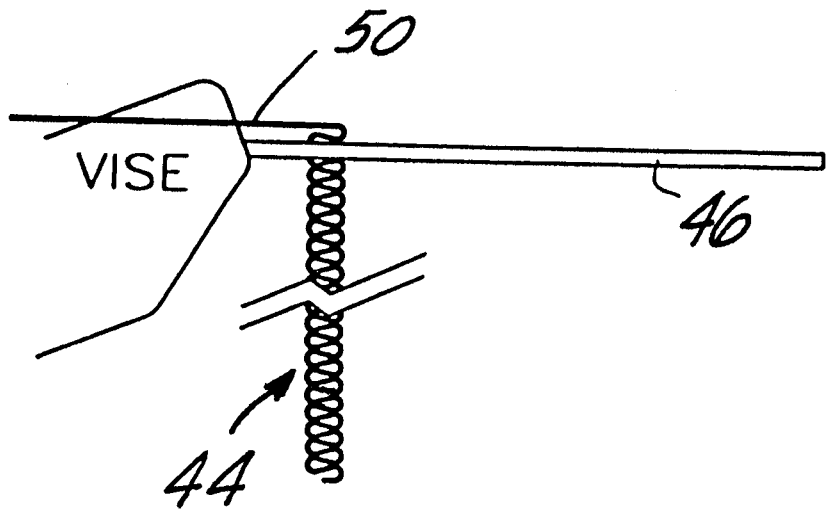

As shown in FIG. 5, the ribbon 44 is held against a mandrel 46. The ribbon 44 is then wrapped around the mandrel. The mandrel 46 will typically range from approximately 30 mils to 90 mils (0.75 to 2.29 mm). At present, the wrapping is done by hand. In order to effect the engagement of the larger amplitude loops, a flat is provided on the mandrel 46 so that the entire ribbon 44 can be slipped under the appropriate loops at each place where loops 34A are to engage one another.

Figure 6:
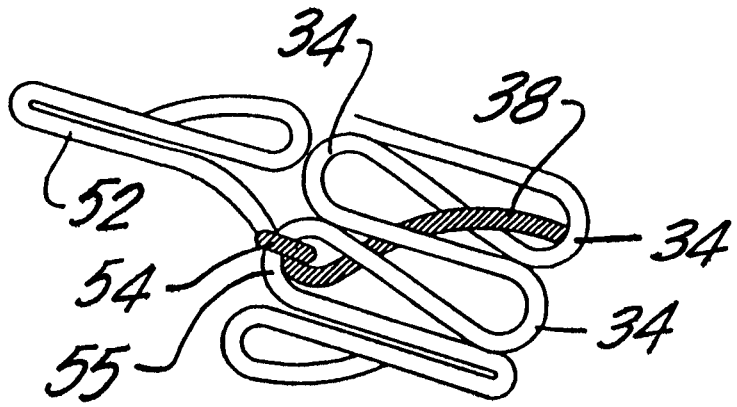
Figure 7:
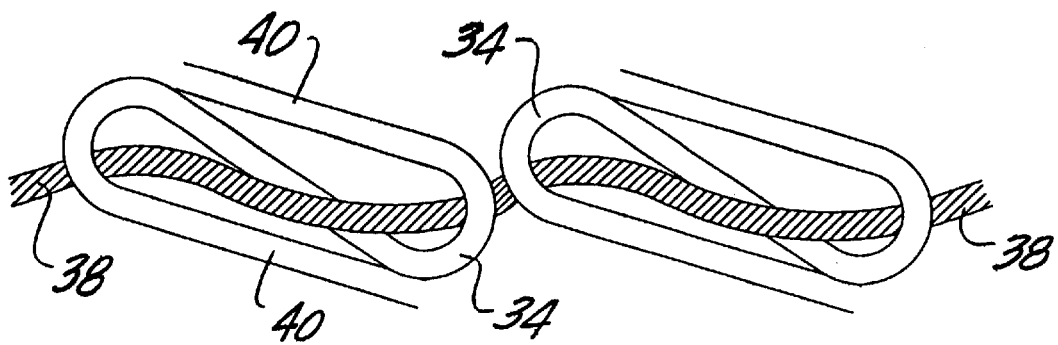

The straight leg 50 of wire that does not form part of the ribbon 44 is used for the spine 38. As shown in FIG. 6, the apex of the first loop 52 is inserted into a predetermined loop to establish a first wrap. The first end knot 54 is created by taking the apex of the first loop 52 and twisting it around the loop 55. The ribbon 44 is then continually wrapped in a single circumferential direction (either clockwise or counterclockwise in a helical fashion around the mandrel to form the stent of desired length. The middle wraps will have predetermined N loops. In the embodiment shown, there are sixteen loops 34 in each middle wrap. The end wraps preferably have fewer loops by two.

Figure 8:
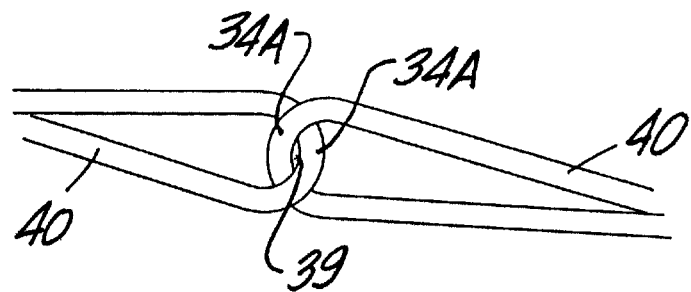
Figure 9:
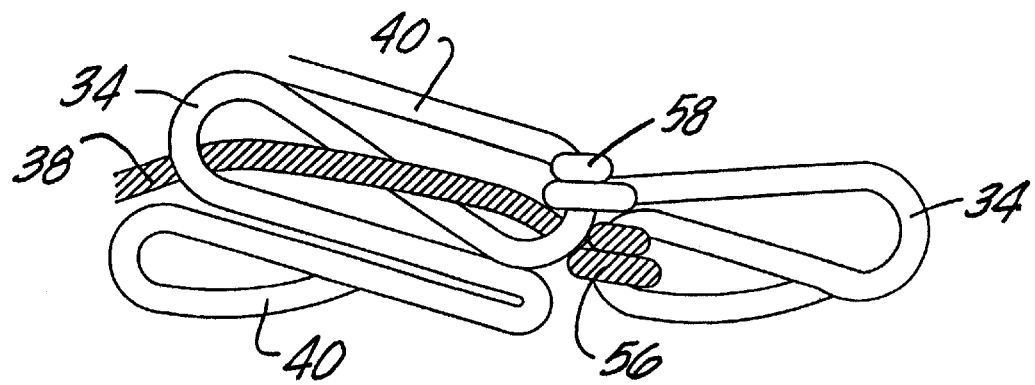

The regularly placed larger amplitude loops 34A will permit the engagement of these larger amplitude loops, as illustrated in FIG. 8.

During the wrapping process, linking the appropriate loops 34A of sequential wraps 32 is accomplished by opening loops of the previous wrap, inserting the end of the ribbon 44 and pulling through until the next sequential ribbon wrap segment is introduced through the opened loops. The appropriate loop apexes are linked together as indicated in FIG. 8. The wire leg 50 that forms the spine 38 is woven through each wrap as the wrap is formed.

When the appropriate number of wraps 32 is completed, the stent is terminated by knot 56 which connects the spine 38 to a loop at the second end of the stent. The knot 58 is created by twisting the last loop of the ribbon 44 around a loop of the last wrap.

Figure 10:
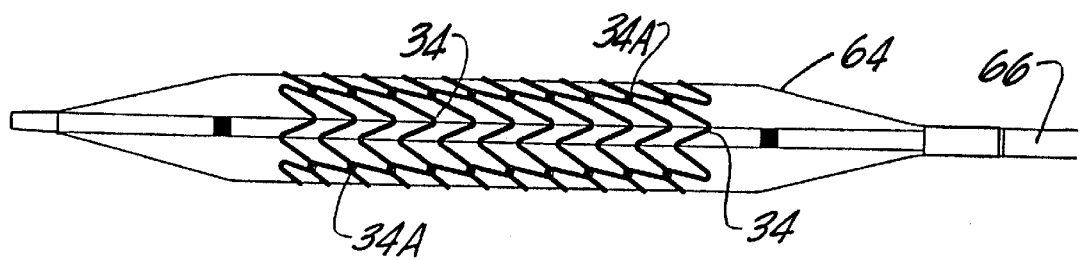
Figure 11:
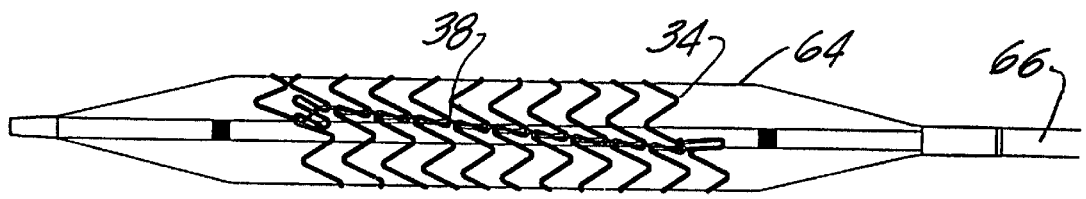

FIGS. 10 and 11 show the stent 30 in an expanded state. When the balloon 64 on a catheter 66 is inflated, the stent 30 moves from the retracted state shown in FIGS. 1 and 2 to the expanded state shown in FIGS. 10 and 11. In FIGS. 10 and 11, the loops 34 are pulled open and have the U-shaped configuration shown.

The Second Stent Embodiment (FIGS. 12–20)

The second stent 70 embodiment has many similarities to the first stent 30 embodiment. Thus those aspects of the discussion of the first stent 30 which are relevant to the stent 70 will not be repeated here. The key difference between the two embodiments is that the wraps 72 in the stent 70 are arranged so that the circumferential center line of each wrap is essentially a circle rather than a portion of a helix. This arrangement is preferable for relatively short stents, such as stents to be placed in ostial locations. Such stents are required on branch lumens that communicate with a more major lumen, such as the intersection of the renal artery with the aorta. In such case, the T-type connection of the lumens requires that the stent in the branch not extend into the main lumen yet cover the side wall of the branch lumen up to the opening into the main lumen. This requires that the end of the stent be a plane perpendicular to the axis of the stent and thus have the configuration shown in FIGS. 12 and 13.

Figure 12:
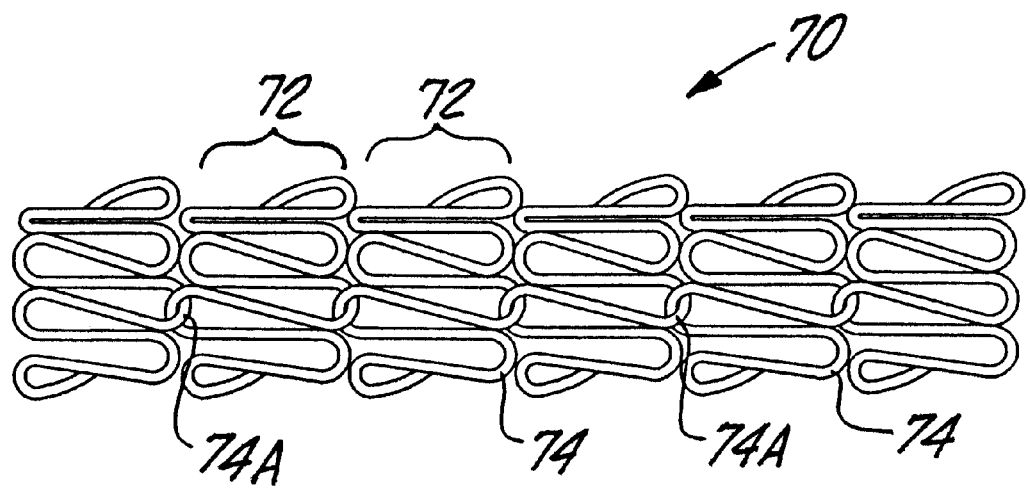
FIGS. 12 through 20 illustrate a circular wrapped linked loop stent.
Figure 13:
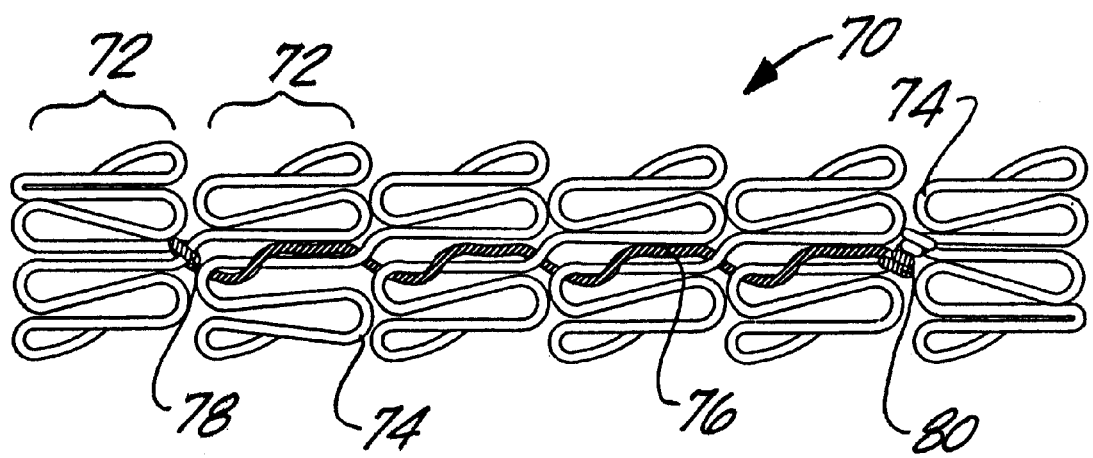

Otherwise the arrangement of FIGS. 12 and 13 is similar to that of FIGS. 1 and 2 including loops 74, engaging loops 74A and a spine 76.

As may be seen in FIG. 13, the knotted ends 78,80 of the spine 76 are located one wrap inwardly from the ends of the stent 70.

Figure 14:
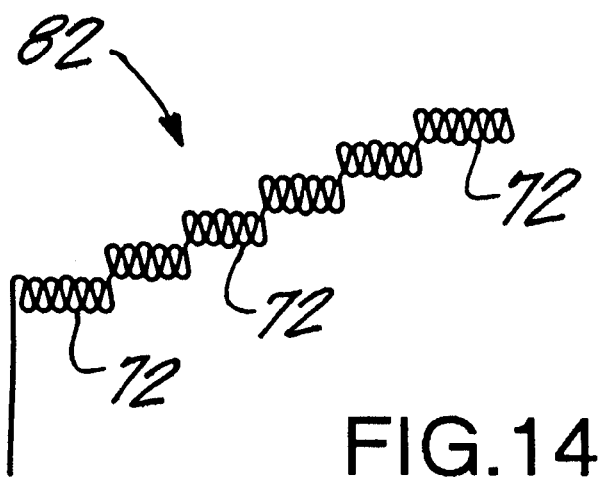
Figure 15:
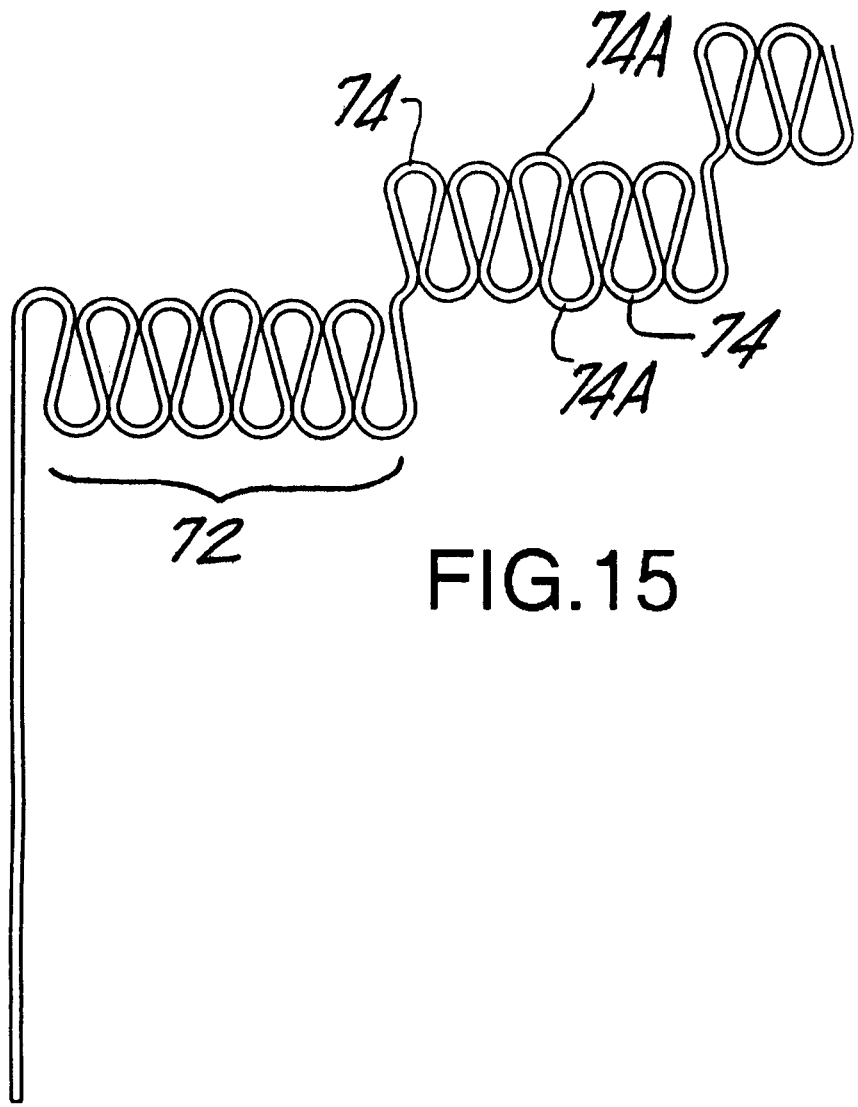

As shown in FIGS. 14 and 15, the ribbon 82 is created in a different fashion than is the ribbon 44 for the stent 30. Essentially, the intermediate ribbon having waves, such shown in FIG. 3, is created by use of a forming block having a stepped interconnected set of U-shaped grooves. Each groove set ultimately forming a single wrap 72. The U-shaped waves are then drawn together manually with the use of tweezers to form the ribbon 82 shown in FIG. 14. A blow-up segment of the ribbon 82 is shown in FIG. 15.

Figure 16:
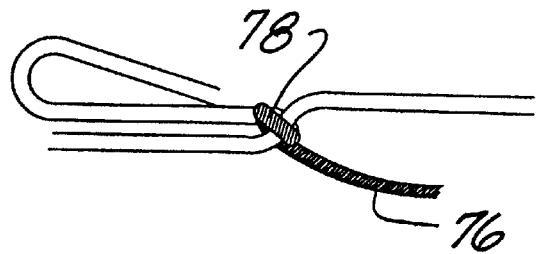

FIG. 16 illustrates that the spine 76 end knot 78 at the first end of the stent 70 is created at the juncture between the first wrap segment and the second wrap segment.

Figure 17:
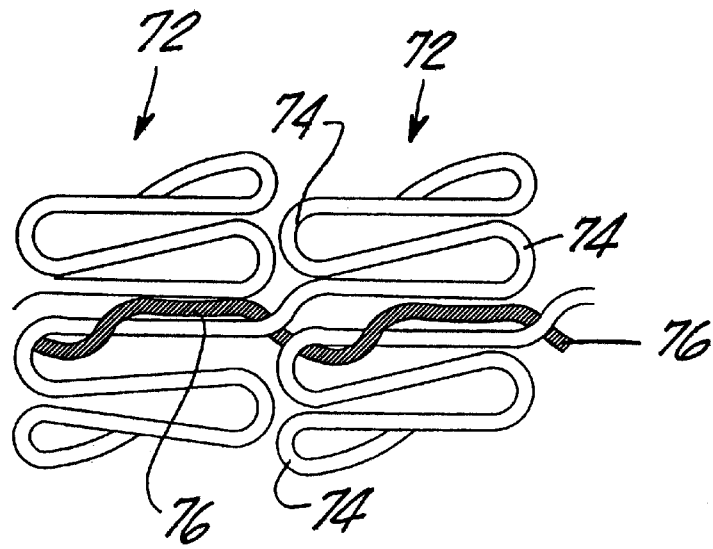

FIG. 17 provides a representation similar to that of FIG. 8 showing the weaving of the spine 76 through longitudinally adjacent loops 74 of separate wraps 72.

Figure 18:
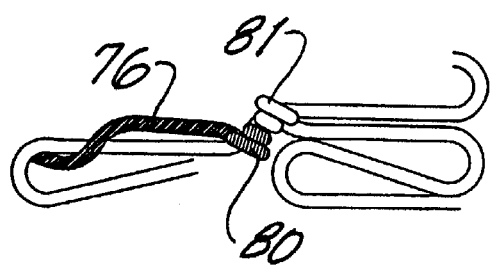

FIG. 18 illustrates the knot 80 at the second end of the stent 70 in which the wire segment that forms the spine 76 is wrapped around the juncture between the last two wraps to/form the knot 80. FIG. 18 also illustrates the knot 81 which terminates the ribbon by wrapping the last loop around the juncture next to the knot 80.

Figure 19:
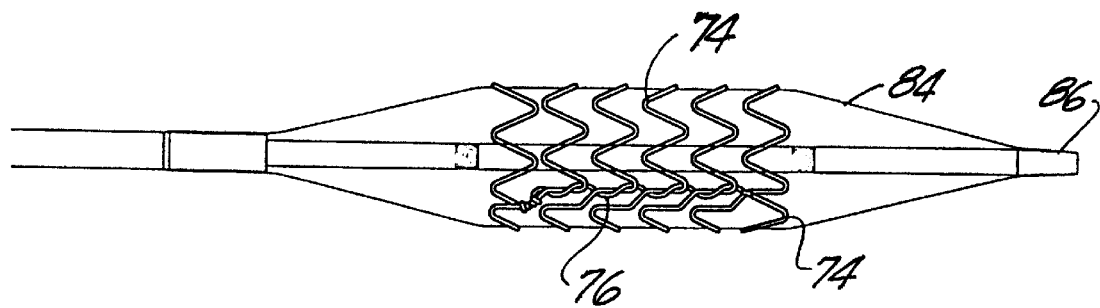
Figure 20:
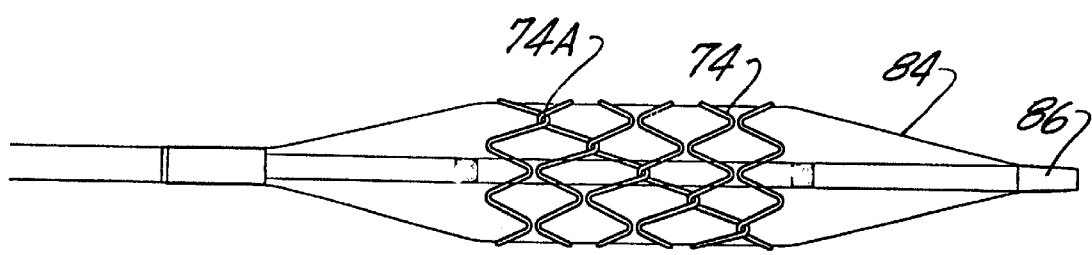

FIGS. 19 and 20 show the stent 70 in an expanded state. When a balloon 84 on a catheter 86 is inflated, the stent 70 moves from the retracted state shown in FIGS. 12 and 13 to the expanded state shown in FIGS. 19 and 20. The tear shape loops of the unexpanded stent, as shown in FIGS. 12 and 13 become, U-shape loops when expanded, as shown in FIGS. 19 and 20.

As can be seen in FIG. 20, the engaging loops 74A do not line up in a longitudinal line but are staggered.

Although two embodiments of this invention have been described, many variations thereon will be obvious to those skilled in this art.

For example, the wire 40 can have a cross-section other than the circular cross-section shown. It could for example be oval or rectangular in cross-section.

The number of engaging loops 34A or 74A can vary in both quantity and geometrical arrangement to provide various degrees of longitudinal structural integrity. The number of engaging loops per wrap will normally be a function of the diameter of the stent.

Although the loops in the stents 30,70 are in a tear drop shape when in the retracted state, it should be noted that these loops assume a U-shape format when in the expanded state. In general, however, the engaging loops can be of any shape that is appropriate for the wrap involved and are not necessarily tear drop shaped when in the retracted state.

The preferred embodiments have been described in which each one of the wraps has at least one of its loops linked to a loop on an adjacent wrap. There might well be circumstances, as for example in a lengthy stent having up to fifty wraps, where certain of the end wraps would not have engaging loops in order to obtain greater flexibility for those ends. What is important is that at least a predetermined zone of the stent will have a loop engagement between each adjacent wrap. It is presently contemplated that this predetermined zone will entail all of the wraps. But as indicated above, there may be circumstances where it will not contain all of the wraps.

In addition, it might be possible to create a partial longitudinal restraint by engaging adjacent loops on only selected ones of the wraps as long as a substantial portion, essentially over fifty percent, of the wraps are so engaged.

It has been found that the extent to which the linked loops will align longitudinally will normally differ when the retracted and the expanded states of the stent are compared. Similarly, the degree to which the spine deviates from being parallel to the axis of the stent normally differs as between the retracted state and expanded state of the stent. The drawings do not necessarily show the extent of these distinctions between retracted and expanded states. However, in the second embodiment 70, the linked loops 74A are shown as longitudinally aligned in the FIG. 12 retracted state and forming a portion of a helix in the FIG. 20 expanded state.

The term wire is used herein to refer to the linear element out of which the loops are formed. It should be understood that the term wire is used to refer to any such linear element no matter how it is created.

For example, it may be created by laser cutting of a flat sheet of appropriate material to directly form the configuration shown in FIG. 3 or in FIG. 4 or in FIG. 14. The term wire is used in the specification and claims to include all such continuous linear elements that have the configuration taught by this patent application.

When the engaging loops 34A, 74A are longitudinally aligned, the stent has less outside or convex flexibility along certain longitudinal lines than along the rest of the longitudinal lines. To maintain a limited degree of outside or convex flexibility along such engaged looped alignments, the engaged loops 34A as shown in FIG. 8 are made to extend more than is necessary to cause engagement. In one embodiment by having the loop create a gap 39, such as shown in FIG. 8, a limited outside or convex flexibility is obtained along the line of the loops without losing the ability of the engaged loops to prevent substantial elongation. In one embodiment, this gap 39 is between 25% to 75% of the wire thickness.

It should be noted that when the stent of this invention is caused to progress through tortuous curves, the stent will rotate to facilitate such progress. The spine will tend to be at the outside or convex curve and the engaged loops will tend to be at the inside or concave curve.

What is claimed is:

1. A radially expandable stent for implantation within a body lumen, comprising:

a set of longitudinally adjacent cylindrical wraps formed from a single wire and wound in a single circumferential direction, each of said wraps being composed of a plurality of loops, over a predetermined zone having multiple wraps, at least one of said loops of each of said wraps in said zone is passed through an adjacent loop of an adjacent one of said wraps thereby linking said at least one of said loops to said adjacent loop to provide a set of linked loops that limit the longitudinal separation of said adjacent wraps relative to one another.

2. The stent of claim 1 wherein:
said linked ones of said loops define a first longitudinal line of said stent, said linked loops permitting substantial longitudinal compression along said first longitudinal line.

3. The stent of claim 1 wherein each of said linked loops has an amplitude greater than the amplitude of the non-linked ones of said loops.

4. The stent of claim 2 wherein each of said linked loops has an amplitude greater than the amplitude of the non-linked ones of said loops.

5. The stent of claim 1 further comprising:
a longitudinal spine woven through said plurality of loops to define a longitudinal line, said spine restraining extension and compression along said longitudinal line, said spine being flexible to permit stent flexibility along said second longitudinal line.

6. The stent of claim 2 further comprising:
a longitudinal spine woven through said plurality of loops to define a second longitudinal line circumferentially spaced from said first longitudinal line, said spine restraining extension and compression along said second longitudinal line, said spine being flexible to permit stent flexibility along said second longitudinal line.

7. The stent of claim 3 further comprising:
a longitudinal spine woven through said plurality of loops to define a second longitudinal line circumferentially spaced from said first longitudinal line, said spine restraining extension and compression along said second longitudinal line, said spine being flexible to permit stent flexibility along said second longitudinal line.

8. The stent of claim 4 further comprising:
a longitudinal spine woven through said plurality of loops to define a second longitudinal line circumferentially spaced from said first longitudinal line, said spine restraining extension and compression along said second longitudinal line, said spine being flexible to permit stent flexibility along said second longitudinal line.

9. The stent of claim 5 wherein said spine is an extension of said wire woven through longitudinally adjacent loops of each of said wraps.

10. The stent of claim 6 wherein said spine is an extension of said wire woven through longitudinally adjacent loops of each of said wraps.

11. The stent of claim 7 wherein said spine is an extension of said wire woven through longitudinally adjacent loops of each of said wraps.

12. The stent of claim 8 wherein said spine is an extension of said wire woven through longitudinally adjacent loops of each of said wraps.

13. The stent of claim 1 wherein the circumferential centerline of said set of wraps is a helix.

14. The stent of claim 4 wherein the circumferential centerline of said set of wraps is a helix.

15. The stent of claim 12 wherein the circumferential centerline of said set of wraps is a helix.

16. The stent of claim 1 wherein the circumferential centerline of said set of wraps is a circle.

17. The stent of claim 4 wherein the circumferential centerline of said set of wraps is a circle.

18. The stent of claim 12 wherein the circumferential centerline of said set of wraps is a circle.

19. A radially expandable stent for implantation within a body lumen, comprising:
a set of longitudinally adjacent cylindrical wraps formed from a single wire and wound in a single circumferential direction,
each of said wraps being composed of a plurality of loops,
over a predetermined zone having multiple wraps, at least one of said loops of each of said wraps in said zone is passed through an adjacent loop of an adjacent one of said wraps thereby linking said at least one of said loops to said adjacent loop to provide a set of linked loops that limit the longitudinal separation of said adjacent wraps relative to one another,
said linked ones of said loops defining a first longitudinal line of said stent, said linked loops permitting substantial longitudinal compression along said first longitudinal line,
each of said linked loops having an amplitude greater than the amplitude of the non-linked ones of said loops, and
a longitudinal spine along a second longitudinal line circumferentially spaced from said first longitudinal line, said spine restraining extension and compression along said second longitudinal line, said spine being flexible to permit stent flexibility along said second longitudinal line.

20. The stent of claim 9, wherein said spine is an extension of said wire woven through longitudinally adjacent loops of each of said wraps.

* * * * *